(12) United States Patent
Hsiung et al.

(10) Patent No.: US 7,435,610 B2
(45) Date of Patent: Oct. 14, 2008

(54) FABRICATION OF ARRAY PH SENSITIVE EGFET AND ITS READOUT CIRCUIT

(75) Inventors: Shen-Kan Hsiung, Jungli (TW); Jung-Chuan Chou, Douliou (TW); Tai-Ping Sun, Jungli (TW); Chung-We Pan, Paotso Village (TW); Jing-Sheng Chiang, Gueishandao (TW)

(73) Assignee: Chung Yuan Christian University, Jungli (TW)

( * ) Notice: Subject to any disclaimer, the term of this patent is extended or adjusted under 35 U.S.C. 154(b) by 441 days.

(21) Appl. No.: 11/342,185

(22) Filed: Jan. 26, 2006

(65) Prior Publication Data

US 2006/0148118 A1    Jul. 6, 2006

Related U.S. Application Data

(63) Continuation-in-part of application No. 10/750,073, filed on Dec. 31, 2003, now abandoned.

(51) Int. Cl.
*H01L 21/00* (2006.01)

(52) U.S. Cl. ............................. 438/48; 438/49; 438/51; 257/252; 257/253

(58) Field of Classification Search ................... 438/48, 438/49, 51, 54; 257/252, 253
See application file for complete search history.

(56) References Cited

U.S. PATENT DOCUMENTS

| 6,414,292 | B1 * | 7/2002 | Afghahi | .................. 250/208.1 |
| 6,703,241 | B1 * | 3/2004 | Sunshine et al. | ............... 436/8 |

* cited by examiner

*Primary Examiner*—Phuc T Dang
(74) *Attorney, Agent, or Firm*—Apex Junis, pllc; Tracy M Heims

(57) ABSTRACT

A method for fabricating an array pH sensor and a readout circuit device of such array pH sensor are implemented by utilizing an extended ion sensitive field effect transistor to construct the array pH sensor and related readout circuit. The structure of the array sensor having this extended ion sensitive field effect transistor comprises a tin dioxide/metal/silicon dioxide multi-layer structure sensor and a tin dioxide/indium tin oxide/glass multi-layer structure sensor and has excellent properties. Furthermore, the readout circuit and the sensor utilize two signal generators for controlling and reading signals. In particular, the sensor can be effective for increasing the accuracy of measurement and reducing the interference of noise.

13 Claims, 7 Drawing Sheets

1cm x 0.2cm

1cm x 0.2cm

FABRICATION OF ARRAY PH SENSITIVE EGFET AND ITS READOUT CIRCUIT

REFERENCE TO PRIOR APPLICATION

This application is a continuation-in-part of prior application Ser. No. 10/750,073, filed Dec. 31, 2003.

BACKGROUND OF THE INVENTION

1. Field of the Invention

This invention relates to a method for fabricating an array pH sensor and a readout circuit of such array pH sensor, and more particularly to a method for fabricating an array pH sensor and a readout circuit of such array pH sensor by utilizing an extended gate ion sensitive field effect transistor (EGFET). The structure of this EGFET in combination with fabrication of biosensors and its readout circuit are produced as an integrated biosensor system. Therefore, the present invention can be applied to some applications such as medical detection, circuit design, semiconductor component fabrication, etc.

2. Description of the Prior Art

Conventional glass electrodes have many advantages such as high linearity, excellent ion selectivity and good stability. However, due to the relatively large volume, high cost and long reaction time, the technologies for fabricating these ion selective glass electrodes have been developed toward the technologies of established silicon semiconductor integrated circuits so as to fabricate field effect sensors. Thus, the conventional glass electrodes are replaced.

In 1970, Piet Bergveld P. in "Development of an ion-sensitive solid-state device for neurophysiological measurements", IEEE Transaction Biomedical Engineering, BME-17, pp. 70-71, 1970, has firstly removed the metal portion from the gate electrode of a general metal oxide semiconductor field effect transistor (MOSFET). Then, the device is dipped into an aqueous solution. With the oxide layer of the sensor's gate electrode serving as an insulating ion sensing membrane, when the transistor is in contact with solutions with different pH values, different potential changes will occur at an interface between the transistor and the solution, such that the current passing through its channel is changed accordingly. In such manner, the pH values or concentrations of other ions can be measured. Thus, this device is referred by Piet Bergveld as a field effect ion sensor.

In 1970's, the studies and the applications of the field effect ion sensors were still under exploration. D. Yu, G. H. Wang, and S. X. Wu, Chemical Sensors, J. Sensor & Transducer Tech., No. 1, pp. 57-62, 1990. However, in 1980's, the studies of the field effect ion sensors were promoted to a new level. The studies about those basic principle researches, crucial technologies or practical applications have been greatly progressed. For example, based on the structure of the ion sensitive field effect transistor, the types of field effect transistor fabricated for measuring a variety of ions and chemical substances had more than 20 or 30. In the aspects of miniaturization, module or multifunction, the component has been greatly developed. See also D. Yu, G. H. Wang, and S. X. Wu, Chemical Sensors, J. Sensor & Transducer Tech., No. 6, pp. 52-60, 1991; D. Yu, G. H. Wang, and S. X. Wu, Chemical Sensors, J. Sensor & Transducer Tech., No. 1, pp. 49-56, 1992; and D. Yu, G. H. Wang, and S. X. Wu, Chemical Sensors, J. Sensor & Transducer Tech., No. 2, pp. 51-55, 1992.

The ion sensitive field effect transistor have been dominated all over the world with several decades of development, because they have the following special features, when compared with the conventional ion selective electrodes. They can be miniaturized to perform microanalysis of solutions. They have high input impedance but low output resistivity. D. Yu, G. H. Wang, and S. X. Wu, Chemical Sensors, J. Sensor & Transducer Tech., No. 1, pp. 57-62, 1990.

Due to the above advantages, many research institutes have been interested in researching the ion sensitive field effect transistor since the past twenty years. Some important researches associated such sensors can be depicted as follows:

(1) miniaturization of reference electrodes (D. Yu, G. H. Wang, and S. X. Wu, Chemical Sensors, J. Sensor & Transducer Tech., No. 3, pp. 53-57, 1991);

(2) differential field effect ion sensor (Gui-Hua Wang, Dun Yu and Yao-Lin Wang, "ISFET temperature characteristics", Sensors and Actuators, 11, pp. 221-237, 1987);

(3) field effect ion sensors having immobile enzyme for detecting function information of organisms, for example glucose concentration, oxygen content in blood, etc. (A. Saito, S. Miyamoto, J. Kimura, T. Kuriyama, "ISFET glucose sensor for undiluted serum sample measurement", Sensors and Actuators B, 5, pp. 237-239, 1992);

(4) exploration of theories, for example adsorptive bonding models;

(5) researches on packaging materials (R. E. G. van Hal, "Characterization and testing of polymer-oxide adhesion to improve the packaging reliability of ISFETs", Sensors and Actuators B, 23, pp. 17-26, 1995);

(6) integration of measurement systems and sensors (B. H. Van Der Schoot, H. H. Van Den Vlekkert, N. F. De Rooij, A Van Den Berg and A. Grisel, "A flow injection analysis system with glass-bonded ISFETs for the simultaneous detection of calcium and potassium ion and pH", Sensors and Actuators B, 4, pp. 239-241, 1991); and (7) researches on simulation of field effect ion sensors (M. Grattarola, "Modeling H+-sensitive FETs with spice", IEEE Transactions on Electron Devices, Vol. 39, NO. 4, pp. 813-819, April 1992).

The extended gate ion sensitive field effect transistor (EGFET) is one of an ion sensitive field effect transistor and firstly introduced by J. Spiegel (J. Van Der Spiegel, I. Lauks, P. Chan, and D. Babic, "The extended gate chemical sensitive field effect transistor as multi-species microprobe", Sensors and Actuators, 4, pp. 291-298, 1983). In contrast to the traditional ion sensitive field effect transistor, the extended gate field effect transistor retains the original metal gate of the metal-insulation layer-semiconductor transistor and the sensitive membrane is deposited on the other end extended from the metal gate. Comparing with the traditional ion sensitive field effect transistor, the extended gate ion sensitive field effect transistor has a lot of advantages, for example (1) the conducting line provides electrostatic protection for the sensor; (2) the transistor of the sensor can prevent direct contact with the aqueous solution; and (3) the influence of light on the sensor is reduced.

The first publication associated to the EGFET is disclosed in 1983 (J. Van Der Spiegel, I. Lauks, P. Chan, and D. Babic, "The extended gate chemical sensitive field effect transistor as multi-species microprobe", Sensors and Actuators, 4, pp. 291-298, 1983). However, the papers published on the international journals are insufficient. After 1986, few researchers published the papers associated to EGFET. Until 1988, our research group proposed an improved EGFET structure, which is divided into two portions, i.e. a sensing portion of $SnO_2/Al/SiO_2$ and a readout circuit portion. L. L. Chi, J. C. Chou, W. Y. Chung, T. P. Sun and S. K. Hsiung, "Study on extended gate field effect transistor with tin oxide sensing membrane", Material Chemistry and Physics, 63 (2000) 19-23.

[14] L. L. Chi, L. T. Yin, J. C. Chou, W. Y. Chung, T. P. Sun, K. P. Hsiung and S. K. Hsiung, "Study on separative structure of EnFET to detect acetylcholine", Sensors and Actuators B, 71, pp. 68-72, 2000.

The patents related to the ISFET are listed hereinafter.

U.S. Patent Publication No. 5,833,824, inventor: Barry W. Benton, date of patent: Nov. 10, 1998, entitled "Dorsal substrate guarded ISFET sensor" disclosed an ion sensitive field effect transistor (ISFET) sensor for sensing ion activity of a solution, wherein the sensor includes a substrate and an ion sensitive field effect transistor. The substrate has a front surface exposed to the solution, a back surface opposite to the front surface and an aperture extending between the front and back surfaces. This patent connects the back surface of the substrate to the front-end sensor through the aperture surface such that only the back surface region is exposed to the solution.

In this study, the word "extended ISFET" and "extended-gate field effect transistor (EGFET)" indicates the same thing. The chemical sensors referenced in this paper were based on the ion sensitive field effect transistors (ISFETs), which were first reported by P. Bergveld [1]. However, the structure of the sensor in the present invention were based on the extended-gate field effect transistor (EGFET), which was first introduced by Van Der Spiegel et al. [2]. The extended-gate filed effect transistor differs from the ISFET in that it was separated into two parts; one was a sensing structure containing a sensitive membrane; the other was a MOSFET structure. The configuration of the extended-gate field effect transistor has several advantages: firstly, it has a lower cost than traditional ion-sensitive field effect transistor; secondly, the transistor could be tested and characterized without the need to contact solutions; thirdly, the device could avoid the influences of temperature and light. The conditions of the disposable biosensor were mass-production and low-cost. Therefore, the extended-gate configuration is useful to develop disposable biosensors for clinical applications.

U.S. Patent Publication No. 6,353,323, inventor: Fuggle; Graham Anthony, Date of patent: Mar. 5, 2002, entitled "Ion concentration and pH measurement" discloses an apparatus and a measuring method for processing the front-end sensor. The front-end ion sensor comprises an ion selective electrode, a reference electrode and an ion sensitive field effect transistor, all of which are immersed in the solution. The sensor is connected to the pre-amplifier, and the reference electrode is connected to the readout circuit so as to separate the sensor from the reference electrode. Accordingly, plural sensor can use a common reference electrode.

U.S. Patent Publication No. 5,350,701, inventor: Jaffrezic-Renault; Nicole; Chovelon; Jean-Marc; Perrot; Hubert; Le Perchec; Pierre; Chevalier; Yves, Date of patent: Sep. 27, 1999, entitled "Process for producing a surface gate of an integrated electrochemical sensor, consisting of a field-effect transistor sensitive to alkaline-earth species and sensor obtained" discloses an improved production process for treating a surface gate comprising a selective membrane as an integrated chemical sensor. A layer of chemically synthesized phosphonate-based is deposited on the gate region of the field-effect ion sensor, and thus the sensing membrane is reactive to alkaline-earth species. This sensor is effective as a detector for measuring concentration of alkaline-earth species, in particular the calcium ion.

U.S. Patent Publication No. 5,319,226, inventor: Sohn; Byung K.; Kwon; Dae H., Date of patent: Jun. 7, 1994, entitled "Method of fabricating an ion sensitive field effect transistor with a $Ta_2O_5$ hydrogen ion sensing membrane" discloses a radio frequency sputtering method for depositing a tantalum oxide film onto a non-conducting silicon nitride film, i.e. onto the gate region of the ion sensor, thereby forming a field-effect ion sensor having the tantalum oxide/silicon nitride/silicon dioxide. The $Ta_2O_5$ film has a thickness of from $40\times10^{-9}$ to $50\times10^{-9}$ m. Then, the resultant film is annealed at an elevated temperature of 375° C. to 450° C. in oxygen gas ambience for about one hour.

U.S. Patent Publication No. 4,657,658, inventor: Sibbald; Alastair, Date of patent: Apr. 14, 1987, entitled "Semiconductor devices" uses a semiconductor integrated circuit for sensing a physico-chemical property of an ambient. The circuit includes a pair of semiconductor devices having a similar geometric and physical structure. Its readout circuits are connected to the same circuit, and the overall structure thereof comprises a metal oxide semiconductor field effect transistor and a field-effect ion sensor so as to construct a differential module system.

U.S. Patent Publication No. 5,922,183, inventor: Rauh; R. David, Date of patent: Jul. 13, 1999, entitled "Metal oxide matrix biosensors" uses a metal oxide-based film as substrate of biological molecules. Such configuration is suitable for developing electrochemical biosensors. The most common metal oxide-based film is a hydrous metal oxide, which can be conductive or semiconductor and have excellent stability against dissolution or irreversible reaction in aqueous and non-aqueous solutions. The metal oxide can be used for both amperometric and potentiometric sensing of enzymes, antibodies, antigens, DNA strands, etc. Iridium oxide is the preferred embodiment of metal oxide film due to the best sensing feature. Furthermore, some other metals, for example Ru, Ti, Pd, Pt, Zr, etc., have similar features and their oxides are very stable against oxidation damage.

The hydrogen ion sensing membrane commonly used on the gate oxide of the field-effect ion sensitive transistor can be selected from silicon dioxide, silicon nitride, tantalum oxide, aluminum oxide, etc., for example. A field-effect ion sensitive transistor with having a hydrogen ion sensing membrane made of tin dioxide is first fabricated in the laboratory. H. K. Liao, J. C. Chou, W. Y. Chung, T. P. Sun and S. K. Hsiung, "Study on the interface trap density of the $SiN_4/SiO_2$ gate ISFET", Proceedings of the 3rd East Asian Conference on Chemical Sensors, Seoul, Korea, November 5-6, pp. 340-400, 1997. The characteristics of this field-effect ion sensitive transistor has an approximate Nernst response in a range of from 56 to 58 mV/pH, a high linear sensitivity, a long-termed stability with low drift, and a low response time of <0.1 second. In addition, the temperature of this sensor can be reduced to zero at an appropriate working current.

Since the ion sensitive field-effect transistor can be used to fabricate array ion sensor array pH sensor by means of the semiconductor fabrication process, the sampling number for detection of the sensor will be increased. The error resulting from one single sensing device can be decreased due to the larger sampling number signals. Thus, when the array sensor is used to measure hydrogen concentration in a human body, the result has a high accuracy and a low error so as to enhance its measuring performance. Furthermore, since the ion sensitive field-effect transistor can be miniaturized, the amount of body fluid to be draw out will be minimized for microanalysis. Due to the rapid reaction time of the ion sensitive field-effect transistor, the array sensor can instantaneously monitor the solution to be measured, thereby reducing measuring time of the tested sample.

Accordingly, the above-described prior art product is not a perfect design and has still many disadvantages to be solved.

In views of the above-described disadvantages resulted from the prior art, the applicant keeps on carving unflaggingly to develop method for fabricating an array pH sensor and a readout circuit device of such array pH sensor according to the present invention through wholehearted experience and research.

SUMMARY OF THE INVENTION

An object of the invention is to provide a method for fabricating an array pH sensor and a readout circuit of such array pH sensor, wherein this fabrication method has a lot of advantages such as simple fabrication equipment, cost effectiveness, mass production, etc. so as to be suitable for fabricating disposable sensors. Therefore, in the field of the array pH sensor, the present invention is highly feasible and applicable.

The method for fabricating an array pH sensor and a readout circuit device of such array pH sensor that can accomplish the above-mentioned objects are implemented by utilizing an extended gate ion sensitive field effect transistor to construct the array pH sensor and related readout circuit. Thus, the present invention is intended to provide an array sensor structure, i.e. a tin dioxide/metal/silicon dioxide multi-layer structure sensor and a tin dioxide/indium tin oxide/glass multi-layer structure sensor, by utilizing such method and device.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

The method for fabricating an array pH sensor and its readout circuit of the present invention are implemented by depositing a non-conductive pH sensing film onto a non-insulated substrate, thereby fabricating a separate array pH sensor and detecting the pH value of the solution by using such array pH sensor. In addition, the readout circuit of this array pH sensor, which includes pre-readout circuit, a multiplexer, a rear end buffer circuit and an amplifier circuit, is fabricated according to the typical processes for making semiconductors. The array pH sensor and the readout circuit can be combined to be a hybrid array pH sensor. The array sensor is advantageous over the single sensing element, because larger sampling signals can decrease error resulting from the sensing element and accuracy thereof is increased. When it is commercialized, the sensor would have high stability and accuracy.

The metal oxide thin-films were prepared by the radio frequency sputtering system ($SnO_2$ target: 99.9%) at a substrate temperature of 150° C. The sensing part of the sensor was based on the $SnO_2$ thin film and the $SnO_2$ thin film was deposited onto the ITO glass by the radio frequency sputtering method. Before depositing the $SnO_2$ thin film, the ITO glasses were washed by methyl alcohol and deionized (D.I.) water. Finally, the device was bounded and packaged to form the $SnO_2$ pH electrode by epoxy.

The extended ISFET can be fabricated when the sensing devices and readout circuits are separated. Additionally, based on the previous reports, several types of sensors were fabricated based on a separated structure, including the pH sensor [3, 4], the acetyicholine sensor [5], the glucose sensor [6] and the pH-sensitive electrode-based urea sensor [7].

As mentioned above, the extended-gate field effect transistor was separated into two parts; one was a sensing structure containing the sensitive membrane and another was a MOSFET structure. Therefore, the circuit part (MOSFET structure) of the sensing structure could be reused and the sensitive membrane part is served as a deposable device. That is to say, the cost of the extended-gate field effect transistor is lower than the ion sensitive field effect transistors.

The process for fabricating the array sensor of the present invention comprises the following steps:

Step 1: providing a p-type silicon substrate with resistivity of 4~7 Ohm-cm and silicon dioxide of 1000 angstrom;

Step 2: growing an Al film by using a metallic mask and a vacuum evaporation machine;

Step 3: growing a $SnO_2$ film by using a metallic mask and a sputter machine; and Step 4: encapsulating the resulting product with epoxy resin.

Figure 14:
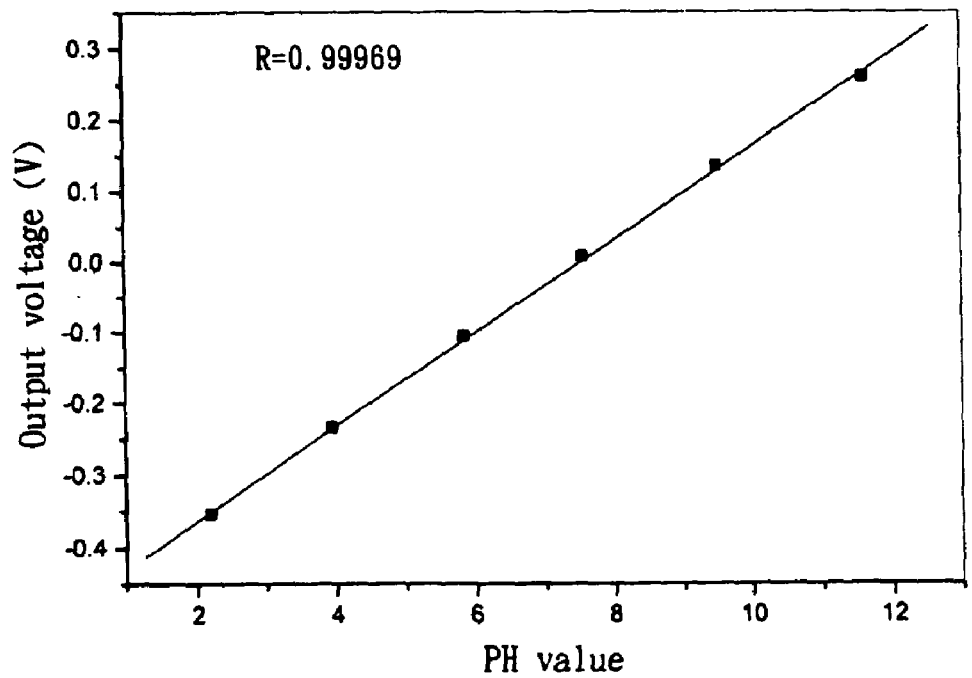
FIG. 14 is a schematic correction curve of the readout signal of the array pH sensor.

The readout circuit portion is fabricated according to a 0.5 micrometer 2P2M n-well process provided by United Microelectronics Corp. (Hsinchu, TW), wherein the related processing conditions are shown in FIG. 14. The features for each layer of the sensor can be illustrated as follows:

1. The thickness of Cpoly is 0.2 micrometer (μm);
2. The thickness of Gpoly is 0.3 micrometer (μm);
3. The thickness of Metal 1 is 0.6 micrometer (μm);
4. The thickness of Metal 2 is 1.1 micrometer (μm);
5. The thickness of Passivation layer is 0.7 micrometer (μm);
6. The thickness of gate oxide layer is 135 angstrom (Å); and
7. The total area of the chip is 1.8 mm².

Figure 1:
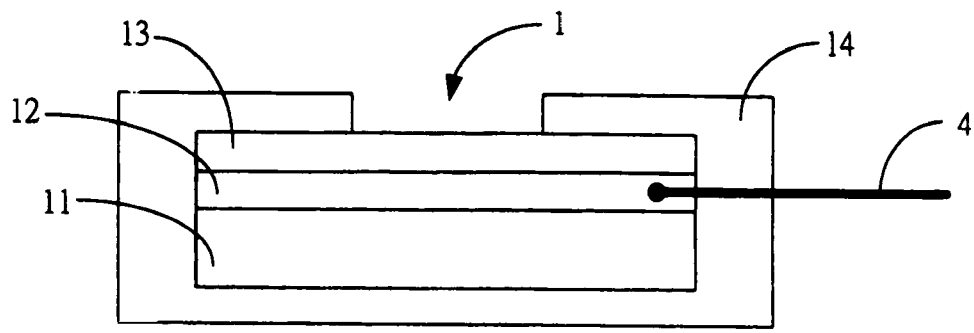
FIG. 1 is the cross-sectional view showing a sensing configuration of $SnO_2/Al/SiO_2/Si$.

FIG. 1 is the cross-sectional view showing a sensing configuration of $SnO_2/Al/SiO_2/Si$. As can be seen in FIG. 1, such structure is easily fabricated according to the standard CMOS fabrication process, and can be a tin dioxide/aluminum metal/silicon dioxide structure 1, which is constructed by depositing an aluminum layer 12 and a tin dioxide layer 13 onto a substrate 11, and encapsulating the resulting structure with epoxy resin 14 to form a opening channel. Via the aluminum layer 12, a conducting line 4 is led out.

Figure 2:
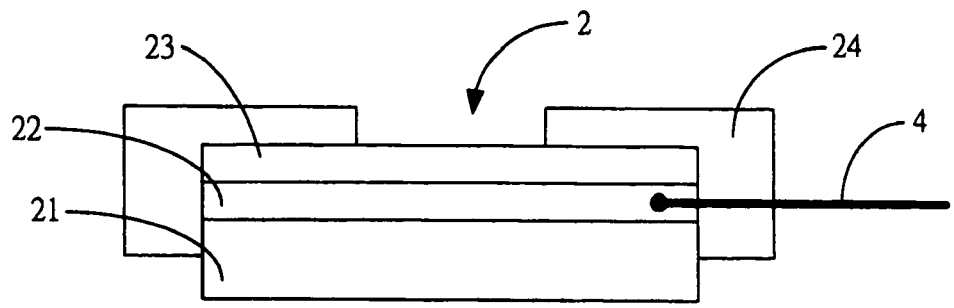
FIG. 2 is the cross-sectional view showing the sensing configuration of $SnO_2/ITO/glass$.

FIG. 2 is the cross-sectional view showing the sensing configuration of $SnO_2$/ITO/glass. Since the glass substrate is cost effective, the sensor with this structure can be applied to fabricate disposable sensors. This structure is a tin dioxide/indium tin oxide/glass structure 2, which is constructed by depositing an indium tin oxide layer 22 and a tin dioxide layer 23 onto a glass substrate 21, and partially encapsulating the resulting structure with epoxy resin 24 to form a opening channel. Via the indium tin oxide layer 22, a conducting line 4 is led out.

Figure 3:
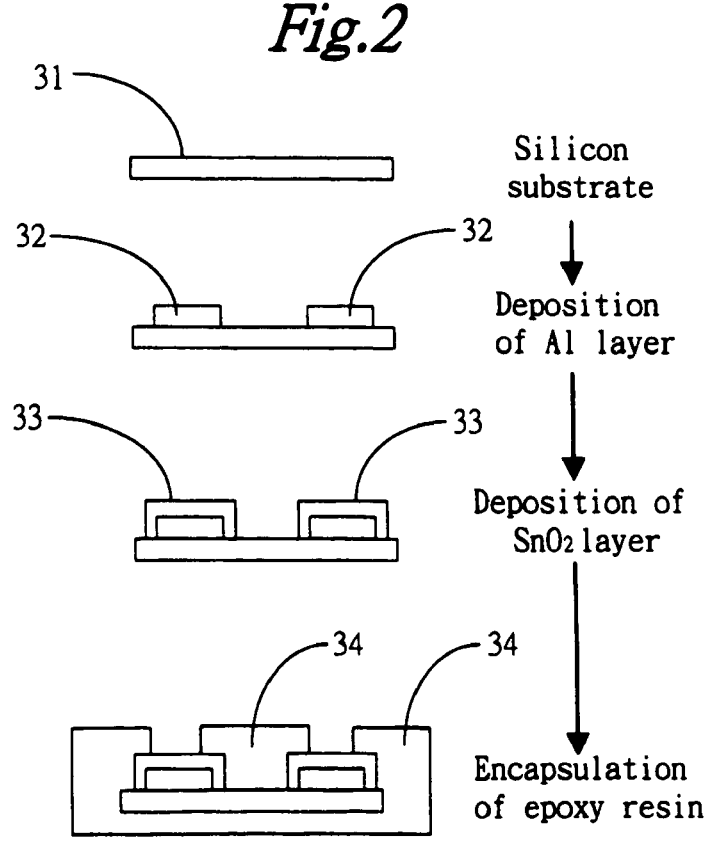
FIG. 3 is a flowchart for fabricating the array pH sensor of the present invention.

Please refer to FIG. 3. The flowchart for fabricating the array pH sensor of the present invention comprises the following steps:

Step 1: providing a silicon substrate 31, for example a p-type silicon substrate with resistivity of 4~7 Ohm-cm and silicon dioxide layer of 1000 angstrom, wherein the silicon substrate can be replaced by glass substrates, ceramic substrates or polymeric substrates in order to broaden the applications of the sensor;

Step 2: growing an Al film 32 by using a metallic mask and a vacuum evaporation machine;

Step 3: growing a $SnO_2$ film 33 by using a metallic mask and a sputter machine; and Step 4: encapsulating the resulting product with epoxy resin 34.

The process for fabricating such sensor is easy because the procedures of coating photoresist solutions and etching films are omitted.

Figure 4:
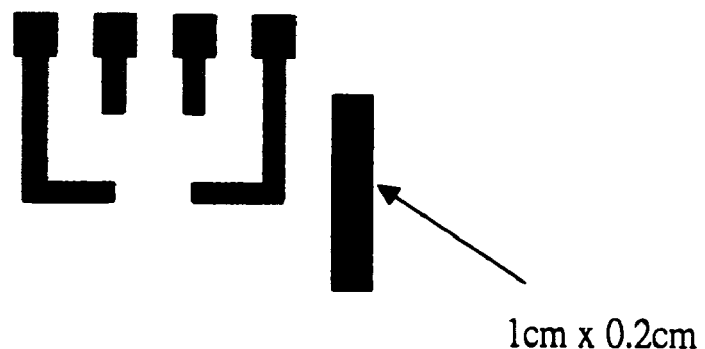
FIG. 4 is a schematic view showing the Al layer mask.

FIG. 4 is a schematic view showing the Al layer mask, which is a metallic mask. The portions of the aluminum film to be deposited are indicated with the black portions. After the metallic mask is etched away, the Al film is deposited onto the metallic portions where the mask has been removed.

Figure 5:
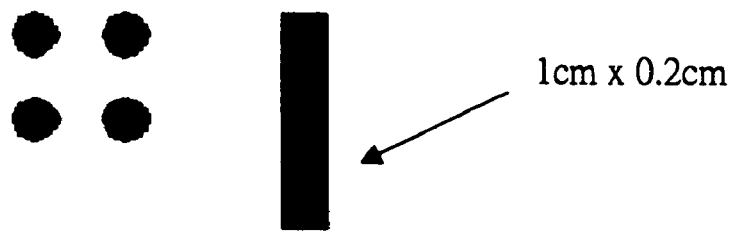
FIG. 5 is a schematic view showing the sensing membrane $SnO_2$ layer mask.

FIG. 5 is a schematic view showing the sensing membrane $SnO_2$ layer mask, which is a metallic $SnO_2$ mask. The portions of the tin dioxide film to be deposited are indicated with the black portions. After the metallic mask is etched away, the tin dioxide film is deposited onto the metallic portions where the mask has been removed.

Figure 6:
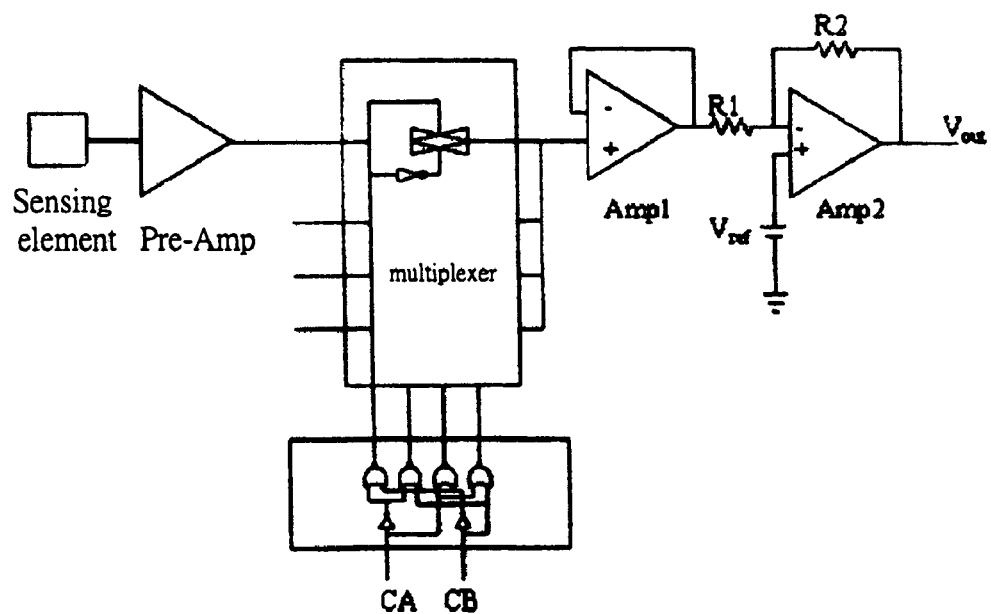
FIG. 6 is the configuration of the array pH sensor of the present invention.

FIG. 6 is the configuration of the array pH sensor of the present invention. This array pH sensor comprises four sensing elements and four pre-amplifiers at the front end thereof. The respective sensing element is read by control circuits, and the pre-amplifier and the control circuits are compensated by the rear end amplifiers, thereby obtaining an output/input ratio of 1. The rear end readout circuit of this array sensor can be used to receive different signals and amplifying these signals for determination. Thus, when the multiplexer is modified, a variety of array sensors can be fabricated for many applications such as fabrication of potentiometric sensor.

Figure 7:
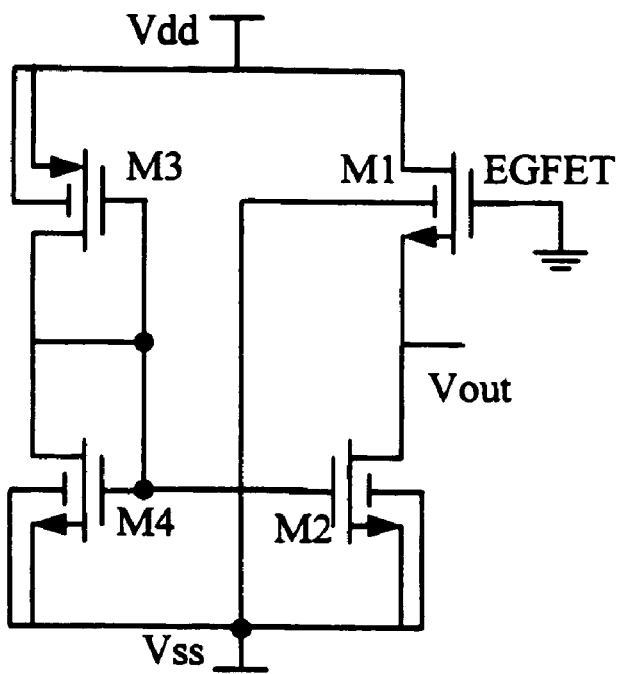
FIG. 7 is the circuit configuration of the pre-amplifier for the array pH sensor.

FIG. 7 is the circuit configuration of the pre-amplifier for the array pH sensor. The pre-amplifier is consisted of four CMOS devices so as to reduce the layout space.

Figure 8:
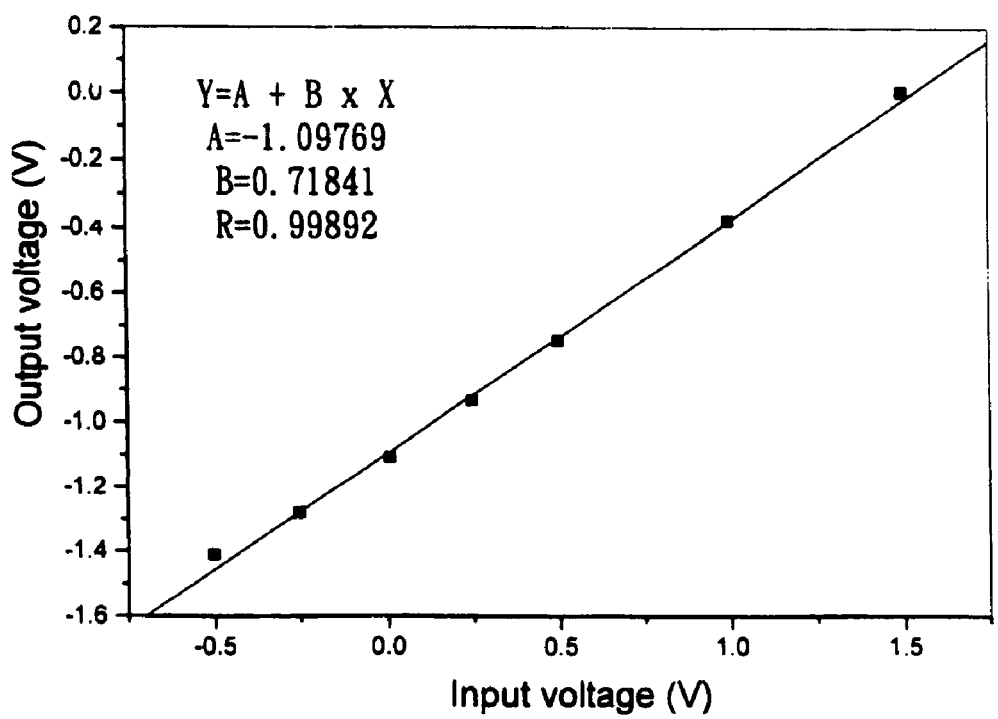
FIG. 8 shows the output/input ratio of the pre-amplifier.

FIG. 8 shows the input/output ratio of the pre-amplifier. The output/input ratio is 0.7184 and an offset voltage is −1.097V. Accordingly, the signal would be decreased, when the sensing element is connected to the pre-amplifier.

Figure 9:
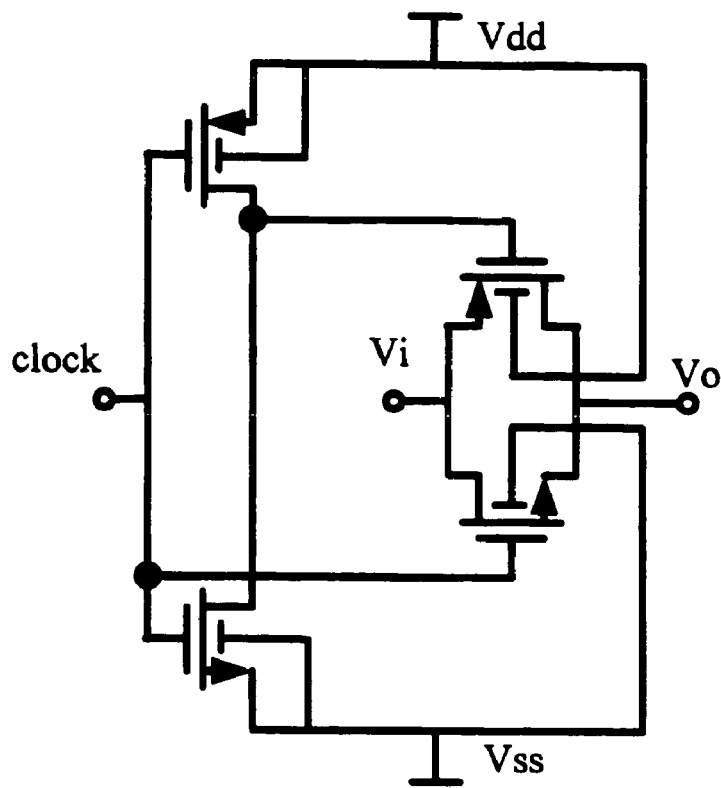
FIG. 9 shows the circuit configuration of the switch of the control portion.

FIG. 9 shows the circuit configuration of the switch of the control portion, which is consisted of an inverter and a CMOS switch.

Figure 10:
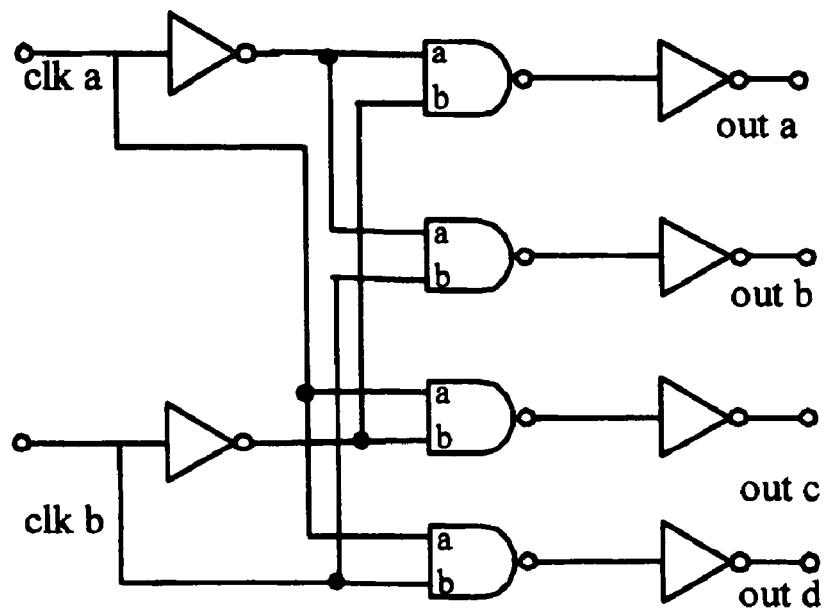
FIG. 10 shows the circuit configuration of a 2 to 4 decoder of the control portion.

FIG. 10 shows the circuit configuration of a 2 to 4 decoder of the control portion, which is consisted of six inverters and four NAND circuits.

Figure 11:
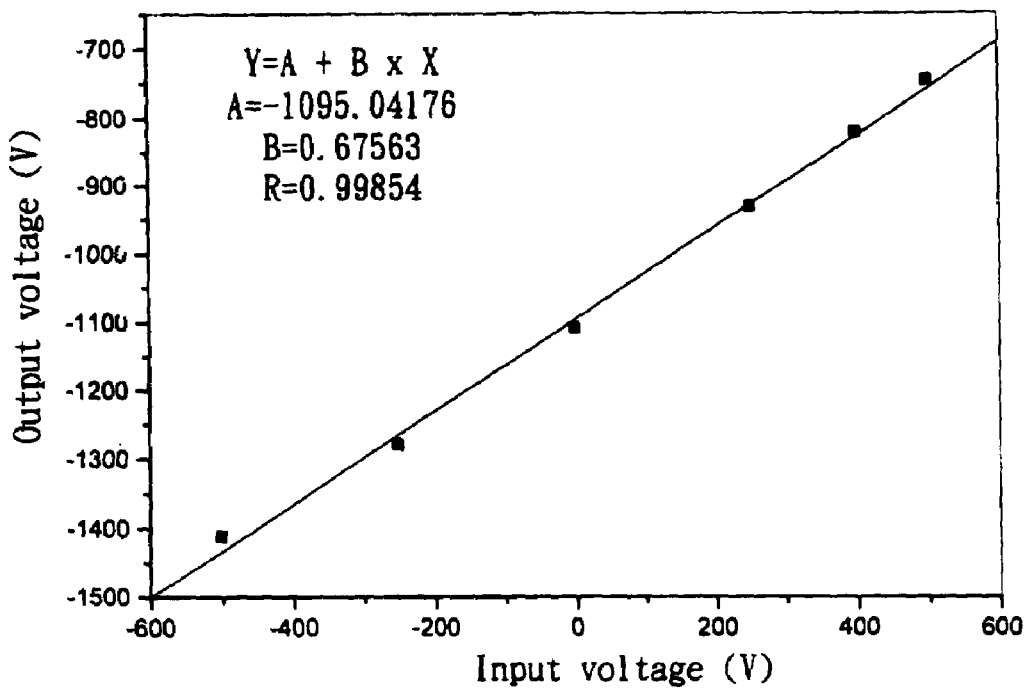
FIG. 11 is a schematic diagram showing the output/input ratio of the circuit combined the pre-amplifier and the control circuit.

FIG. 11 is a schematic diagram showing the output/input ratio of the circuit combined the pre-amplifier and the control circuit. The output/input ratio is 0.675 and the offset voltage is −1.095V. Accordingly, the signal would be further decreased, when the sensing element was connected to the pre-amplifier and multiplexer.

Figure 12:
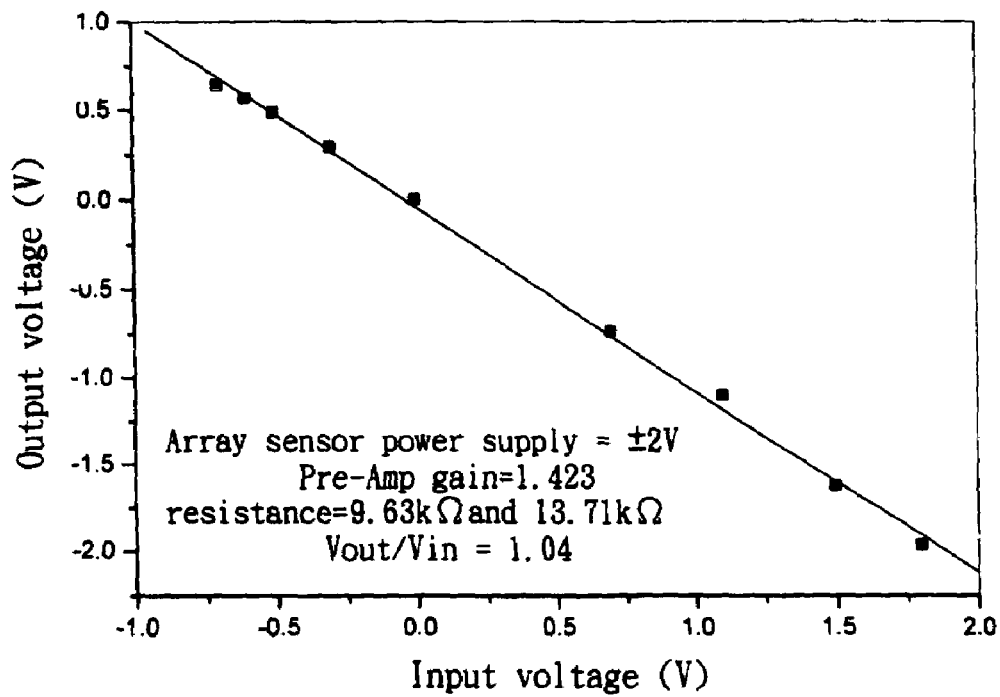
FIG. 12 is a schematic diagram showing the output/input ratio of the circuit of the array pH sensor.

FIG. 12 is a schematic diagram showing the output/input ratio of the circuit of the array pH sensor. As can be seen in FIG. 12, due to the amplification of the rear end readout circuit, the signals of the sensing membrane can be compensated to the initial values and the ratio of the output voltage to the input voltage is 1.04.

It was in order to compensate the decreasing of pre-circuit. So, The input output ratio is 1.04 of the array pH sensor system, when the circuit included the pre-amplifier, multiplexer, buffer and post amplifier.

Figure 13:
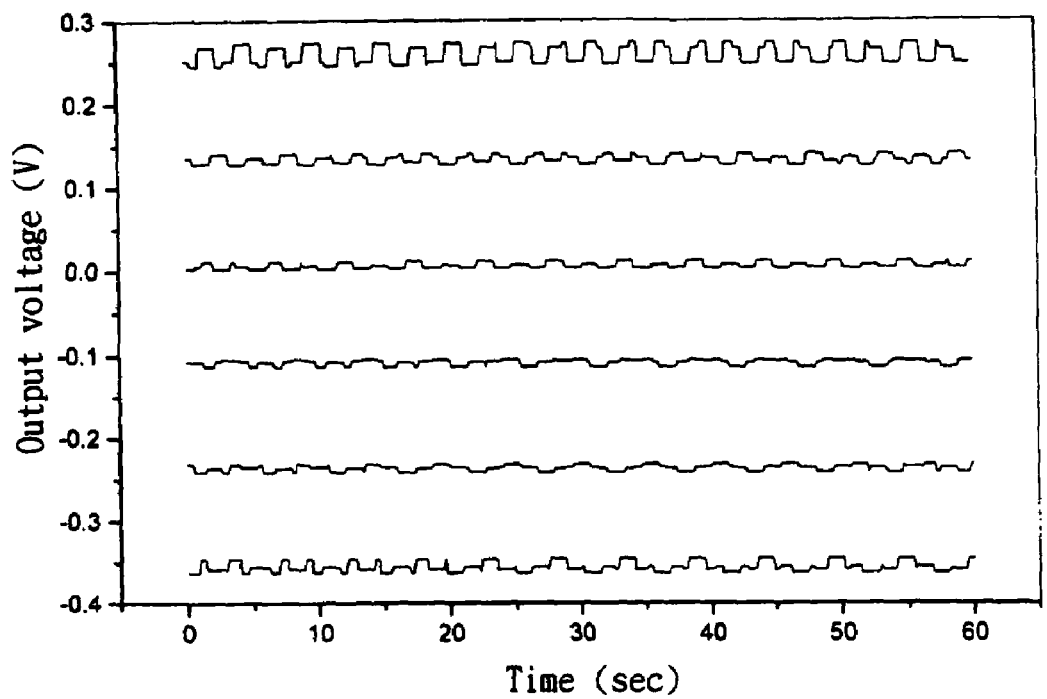
FIG. 13 is a schematic diagram showing the readout signal of the array pH sensor.

FIG. 13 is a schematic diagram showing the readout signal of the array pH sensor. As can be seen in FIG. 13, four sets of signals are stable, indicating a stable fabrication process of this array sensor.

FIG. 14 is a schematic correction curve of the readout signal of the array pH sensor. The correction curve shows a linear pH sensitivity of 0.99969, which indicates an excellent performance of the array ion sensor.

Figure 15:
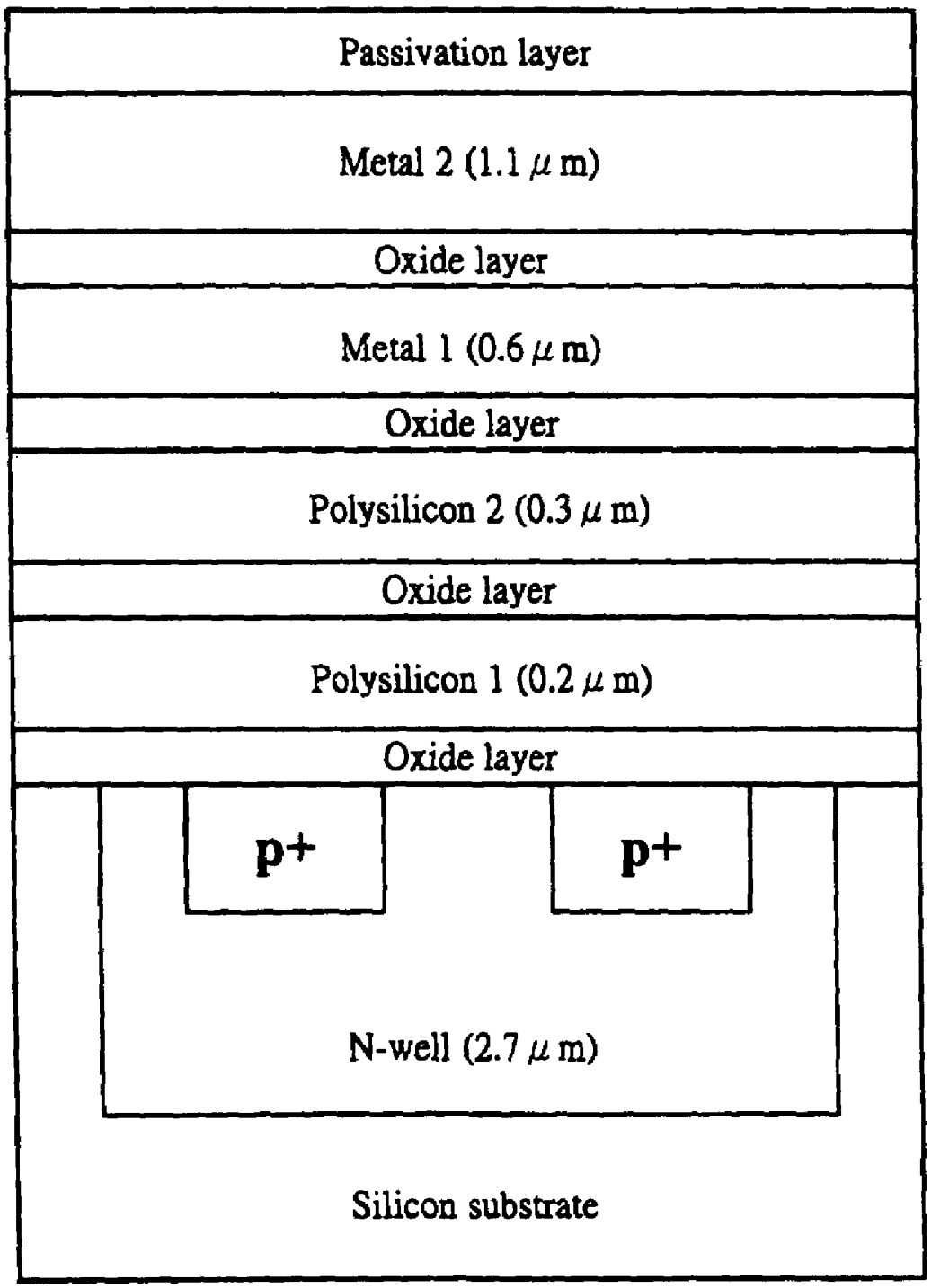
FIG. 15 is a cross-section view showing the related processes for fabricating a chip.

FIG. 15 is a cross-section view showing the related processes for fabricating a chip. In FIG. 15, the relative positions of the layer structures of a 0.5 micrometer n-well double polysilicon double-metal process are shown.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for fabricating an array pH sensor and a readout circuit device of said array pH sensor, comprising:

depositing a non-conductive pH sensing film onto a non-insulated substrate, thereby fabricating a separate array pH sensor and detecting the pH value of the solution by using said array pH sensor to separate the sensor and the general metal oxide semiconductor field effect transistor;

fabricating said readout circuit device of said array pH sensor according to a conventional processes for making semiconductors; and combining said array pH sensor and said readout circuit device as a hybrid array pH sensor.

2. The method for fabricating an array pH sensor and a readout circuit device of said array pH sensor according to claim 1, wherein said array pH sensor is fabricated by the following steps:

Step 1: providing a substrate;

Step 2: growing an Al film by using a metallic mask and a vacuum evaporation machine;

Step 3: growing a $SnO_2$ film by using a metallic mask and a sputter machine; and Step 4: encapsulating the resulting product with epoxy resin.

3. The method for fabricating an array pH sensor and a readout circuit device of said array pH sensor according to claim 1, wherein said array pH sensor has a tin dioxide/metal/silicon dioxide multi-layer structure or a tin dioxide/indium tin oxide/glass multi-layer structure.

4. The method for fabricating an array pH sensor and a readout circuit device of said array pH sensor according to claim 1, wherein said array pH sensor comprises a pre-readout circuit, a multiplexer, a rear end buffer circuit and an amplifier circuit.

5. The method for fabricating an array pH sensor and a readout circuit device of said array pH sensor according to claim 2, wherein said substrate is selected from a glass substrate, a silicon substrate, a ceramic substrate or a polymeric substrate.

6. The method for fabricating an array pH sensor and a readout circuit device of said array pH sensor according to claim 3, wherein said tin dioxide/metal/silicon dioxide structure is formed by depositing an aluminum layer and a tin dioxide layer onto said substrate, and encapsulating the resulting structure with epoxy resin to form a opening channel, wherein a conducting line is led out via said aluminum layer.

7. The method for fabricating an array pH sensor and a readout circuit device of said array pH sensor according to claim 3, wherein said tin dioxide/indium tin oxide/glass is formed by depositing an indium tin oxide layer and a tin dioxide layer onto said substrate, and encapsulating the resulting structure with epoxy resin to form a opening channel, wherein a conducting line is led out via said indium tin oxide layer.

8. The method for fabricating an array pH sensor and a readout circuit device of said array pH sensor according to claim 4, wherein said readout circuit device of said array pH sensor receives different signals and amplifies these signals for determination such that when the multiplexer is modified, a variety of array sensors can be fabricated and said array sensor can be applied for fabrication of potentiometric sensor.

9. The method of fabricating an array pH sensor and a readout circuit device of said array pH sensor according to claim 1 whereby the pH sensor and the general metal oxide semiconductor field effect transistor are separated and are prepared by taking metal oxide thin-films and depositing said film on an ITO glass by a radio frequency sputtering method, and then binding with epoxy.

10. The method of fabricating an array pH sensor and a readout circuit device of said array pH sensor according to claim 9 wherein said sensing part of sensor is based on an $SnO_2$ thin film.

11. The method of fabricating an array pH sensor and a readout circuit device of said array pH sensor according to claim 9 wherein said radio frequency sputtering method has an $SnO_2$ target of 99.9% at a substrate temperature of 150° C.

12. The method of fabricating an array pH sensor and a readout circuit device of said array pH sensor according to claim 9 wherein said ITO glass is prepared by washing with methyl alcohol and deionized water.

13. The method of fabricating an array pH sensor and a readout circuit device of said array pH sensor according to claim 1 whereby the separate array pH sensing film is fabricated by depositing said Al onto an Si substrate, depositing $SnO_2$ on to said Si substrate and packaging with epoxy.

* * * * *